(12) United States Patent
Kohnke

(10) Patent No.: US 8,802,141 B2
(45) Date of Patent: Aug. 12, 2014

(54) AGENT DELIVERY SYSTEM

(76) Inventor: John Kohnke, Nelson (AU)

( * ) Notice: Subject to any disclaimer, the term of this patent is extended or adjusted under 35 U.S.C. 154(b) by 1697 days.

(21) Appl. No.: 10/515,002

(22) PCT Filed: May 20, 2003

(86) PCT No.: PCT/AU03/00596
§ 371 (c)(1),
(2), (4) Date: Aug. 4, 2005

(87) PCT Pub. No.: WO03/097016
PCT Pub. Date: Nov. 27, 2003

(65) Prior Publication Data
US 2006/0088597 A1    Apr. 27, 2006

(30) Foreign Application Priority Data
May 20, 2002   (AU) ...................................... PS2440

(51) Int. Cl.
*A61K 9/20*       (2006.01)
*A61K 8/81*       (2006.01)
*A61K 31/74*      (2006.01)
*A23L 1/16*       (2006.01)

(52) U.S. Cl.
USPC ..... 424/464; 424/70.15; 424/501; 424/78.03; 424/78.08; 426/557

(58) Field of Classification Search
None
See application file for complete search history.

(56) References Cited

U.S. PATENT DOCUMENTS

| | | | |
|---|---|---|---|
| 2,685,517 A | | 8/1954 | Dunmire |
| 4,308,252 A | | 12/1981 | Tomaich et al. |
| 4,495,177 A | | 1/1985 | Taracatac et al. |
| 4,627,980 A | * | 12/1986 | Lynch ............................ 424/54 |
| 5,030,463 A | | 7/1991 | Evans |
| 5,057,305 A | | 10/1991 | Aberg |
| 5,188,825 A | | 2/1993 | Iles et al. |
| 5,262,167 A | | 11/1993 | Vegesna et al. |
| 5,320,848 A | | 6/1994 | Geyer et al. |
| 5,597,844 A | | 1/1997 | Chauhan et al. |
| 5,624,906 A | * | 4/1997 | Vermeer ........................ 514/23 |
| 5,633,005 A | | 5/1997 | Imer |
| 5,686,107 A | | 11/1997 | Ratnaraj et al. |
| 5,708,017 A | * | 1/1998 | Dave et al. .................... 514/393 |
| 5,834,496 A | | 11/1998 | Young |
| 6,258,846 B1 | | 7/2001 | Hermelin et al. |
| 2003/0124183 A1 | * | 7/2003 | Sowden ........................ 424/464 |

FOREIGN PATENT DOCUMENTS

| | | |
|---|---|---|
| EP | 0 127 400 | 12/1984 |
| EP | 0 419 275 | 3/1991 |
| EP | 0 435 684 A | 7/1991 |
| EP | 0 471 967 A | 2/1992 |
| EP | 0 487 774 A | 6/1992 |
| EP | 0 492 235 A | 7/1992 |
| WO | WO 94/12180 | 6/1994 |
| WO | WO 94/14422 | 7/1994 |
| WO | WO 95/10195 | 4/1995 |
| WO | WO 96/37118 | 11/1996 |
| WO | WO 9736572 A1 * | 10/1997 |
| WO | WO 99/26488 | 6/1999 |
| WO | WO 99/33445 | 7/1999 |
| WO | WO 9933445 A1 * | 7/1999 |
| WO | WO 99/48809 | 9/1999 |
| WO | WO 00/48613 | 8/2000 |

OTHER PUBLICATIONS

Ott, E.A. and Asquith, R. L. "Trace Mineral Supplementation of Yearlings Horses", *Journal of Animal Science*, 1995, vol. 72(2), pp. 466-471.
Harris, P.A. "Developments in the Equine Nutrition: Comparing the Beginning and the End of This Century", J. Nutr., Dec. 1998, 128 (12 Suppl), pp. 2698S-2703S.
Notice of Acceptance for corresponding Australian Application, AU 2002332990.
Notification of Grant for corresponding British application, GB 2406518.
U.S. Appl. No. 10/493,741, filed Jan. 2005, Kohnke, 2005-0019390, Mar. 7, 2008 Non-Final Office Action Oct. 21, 2008 Final Office Action.
Rossander-Hulten et al. "Competitive inhibition of iron absorption by manganese and zinc in humans", Am. J. Clin. Nutr., 1991, 1, 152-156.
Wikipedia "Polyvinylpyrrolidone", http://en.wikipedia.org/wiki/Polyvinylpyrrolidon, downloaded Mar. 31, 2011; htt.

* cited by examiner

*Primary Examiner* — Michael G Hartley
*Assistant Examiner* — Nabila Ebrahim
(74) *Attorney, Agent, or Firm* — Knobbe Martens Olson & Bear LLP

(57) ABSTRACT

A delivery vehicle including a mixture of: a) an effective amount of an expander activatable by a wetting agent and, b) a treatment agent. The expander and treatment agent intermingled and compressed so as to form a substantially solid delivery vehicle. The solid delivery vehicle, on exposure to a volume of wetting agent forms a predetermined volume of a paste containing the treatment agent; and the volume of paste is adapted for delivery of the treatment agent.

15 Claims, 2 Drawing Sheets

AGENT DELIVERY SYSTEM

RELATED APPLICATIONS

This application is a national phase entry in the United States of the International Application PCT/AU03/00596 filed May 20, 2003 and claims the benefit of the Australian application PS 2440 filed May 20, 2002.

The present invention relates to a method and apparatus for the application of treatment agents, and more particularly to treatment agents delivered by a vehicle in the form of a paste.

BACKGROUND

Treatment agents delivered by a vehicle in the form of paste exist for applications in the areas of therapeutics, nutrition, hygiene and cosmetics. A paste generally demands complicated and bulky packaging such as pressure packs, tubes, jars and the like and may, in the case of open topped containers, suffer from limited viability over time.

It is an object of the present invention to address or ameliorate at least one of the above disadvantages or to provide a useful alternative.

BRIEF DESCRIPTION OF INVENTION

Accordingly, in one broad form of the invention there is provided a delivery vehicle comprising a mixture of:
a. an effective amount of an expander activatable by a wetting agent,
b. a treatment agent;
said expander and treatment agent intermingled and compressed so as to form a substantially solid delivery vehicle; said solid delivery vehicle, on exposure to a volume of wetting agent forming a predetermined volume of a paste containing said treatment agent; said volume of paste adapted for delivery of said treatment agent.

Preferably said wetting agent is water.
Preferably said wetting agent activatable expander comprises granules of a cross-linked homopolymer of N-vinyl-2-pyrrolidone.
Preferably said granules have an average maximum dimension in the range of 10-100 µm.
Preferably said granules have an average maximum dimension in the range of 20-80 µm.
Preferably said granules have an average maximum dimension in the range of 30-60 µm.
Preferably said expander comprises 20-60% by weight of said vehicle.
Preferably said expander comprises 30-50% by weight of said vehicle.
Preferably said expander comprises 40-50% by weight of said vehicle.
Preferably said expander to the total combined weight of said vehicle is determined by the desired volume of the paste
Preferably the treatment agent is therapeutic.
Preferably the treatment agent is nutritional.
Preferably the treatment agent is hygienic.
Preferably the treatment agent is cosmetic.
Preferably the treatment agent is injected.
Preferably the treatment agent is applied topically.
Preferably the treatment agent is ingested.

In a further broad form of the invention there is provided a method of delivery of a treatment agent as outlined above, wherein said volume of paste formed from the solid delivery vehicle is adapted to designated delivery devices.

Preferably said delivery device is a syringe.
Preferably said solid delivery vehicle is placed in said syringe.
Preferably water is drawn into the syringe.
Preferably said water reacts with said solid delivery vehicle to form a paste.
Preferably the syringe is of a prescribed volume.
Preferably the paste formed is adapted to fill the syringe.
Preferably said delivery device is a spoon.
Preferably said solid delivery vehicle is placed in the bowl of a spoon.
Preferably said spoon is filled with water.
Preferably said water reacts with said solid delivery vehicle to form a paste.
Preferably the spoon is of a standard designation.
Preferably the paste formed is adapted to fill the bowl of the spoon.
Preferably said delivery mode is a medicine glass.
Preferably said solid delivery vehicle is placed in said medicine glass.
Preferably said medicine glass is filled with water to a predetermined volume.
Preferably said water reacts with said solid delivery vehicle to form a paste.
Preferably the volume of the paste is adapted to its treatment function.

In yet a further broad form of the invention there is provided a method for the delivery of a treatment agent wherein said treatment agent is stored and transported in the form of a solid delivery vehicle prior to use; said solid delivery vehicle being transformed into a paste when required for application.

Preferably said treatment agent is in the form of a tablet.
Preferably said tablet is adapted for insertion into a syringe.
Preferably said tablet is adapted for placement in a spoon.
Preferably said tablet is adapted for placement on a shaving brush.
Preferably said tablet is adapted for placement on a toothbrush.
Preferably said tablet is adapted for placement in the palm of the hand.
Preferably said tablet is adapted for placement in a medicine glass.
Preferably said transformation of solid delivery vehicle into said paste is mediated by water.
Preferably the said transformation of solid delivery vehicle into a paste is effected at the location of application.

BRIEF DESCRIPTION OF THE DRAWINGS

Embodiments of the present invention will now be described with reference to the accompanying drawings wherein.

DETAILED DESCRIPTION OF PREFERRED EMBODIMENTS

In a preferred embodiment of the present invention there is provided a vehicle for a treatment agent in a first form as a solid delivery vehicle and in a second derived form as a paste. The solid form of the delivery vehicle is produced by the process of cold pressing having a variety of shapes. Preferably the choice of shapes is predicated on the intended use of the solid delivery vehicle. As examples, chosen shapes may include spheres, caplets, bars, domes and toroidal shapes.

Preferably solid delivery vehicles are composed of treatment agents formulated to suit the intended end use of a particular solid delivery vehicle. Thus solid delivery vehicles may include medicinal, nutritional, hygiene or cosmetic agents as their use directed ingredients.

In addition to use directed ingredients, solid delivery vehicles include 30-65% by volume a paste-inducing compound, preferably granules of N-vinyl-2-pyrrolidone commonly known under the registered name of Polyplasdone® having an average maximum dimension in the range of 10-100 μm.

Preferably solid delivery vehicles may also contain colouring, flavouring, antioxidizing and preserving agents and the like depending on intended use. For example a solid delivery vehicle intended for treatment of a medical condition in a particular animal or human may in addition to its medicinal and paste-inducing ingredients include flavouring agreeable to the intended animal or human vector.

Figure 1:
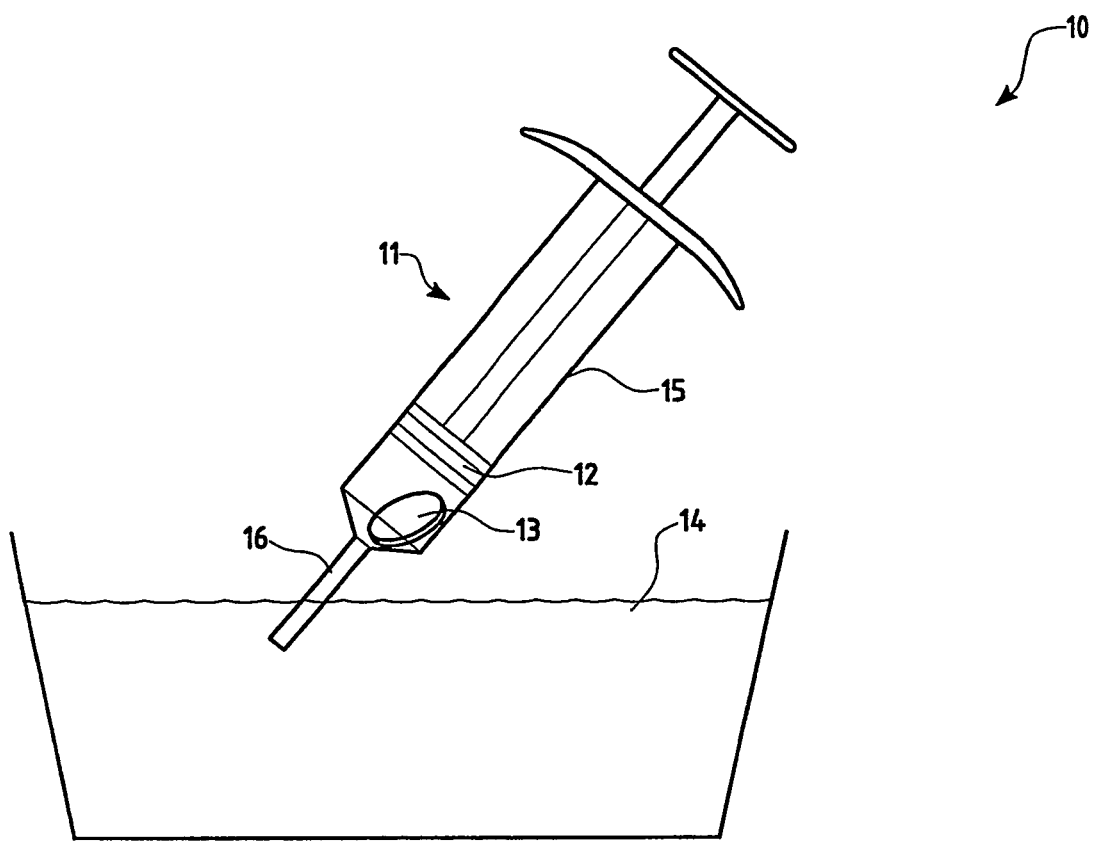
FIG. 1 illustrates an application method according to a first embodiment of the invention.

A first preferred method of application of a solid delivery vehicle according to the invention will now be described with reference to FIG. 1. Application method 10 includes a syringe 11 adapted to discharge a paste through nozzle 16. A solid delivery vehicle 13 is placed into the syringe barrel 15 and piston 12 retracted to draw water 14 through nozzle 16 into the barrel 15. The water entering the barrel reacts with the paste-inducing compound of the solid delivery vehicle 13 to form a paste within barrel 15. The paste may now, for example, be conveniently introduced into an animal by means of syringe 11. Clearly the paste may also be extruded from the syringe to be applied to an animal's coat or skin.

In this embodiment solid delivery vehicle 13 is shaped to suit a designated syringe diameter and its paste-inducing compound dosed to the syringe volume, that is to say the volume of water which may be drawn into the syringe dissolves the solid into a paste equal in volume to that of the syringe barrel. Thus for example a solid delivery vehicle constituted to treat a particular condition in an animal such as a horse will be directed for use with a standard 10 mL dosing syringe.

Figure 2:
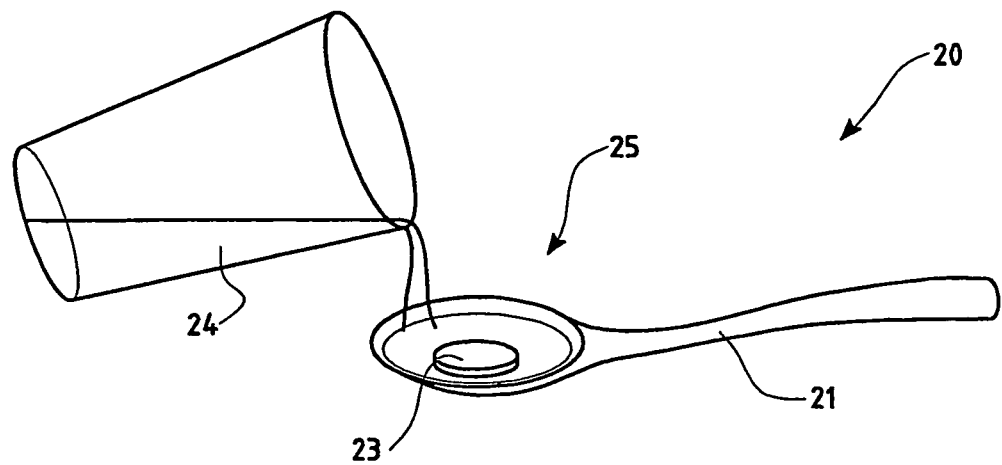
FIG. 2 illustrates an application method according to a second embodiment of the invention.

With reference to FIG. 2, a second preferred embodiment of the invention 20 comprises a solid delivery vehicle 23 adapted to spoon volume 25. In this embodiment the dosage of paste-inducing compound is adapted to the standard spoon measures such as teaspoon and tablespoon. When water 24 is added to the spoon and solid delivery vehicle 23, the paste thereby induced fills the spoon volume.

Figure 3:
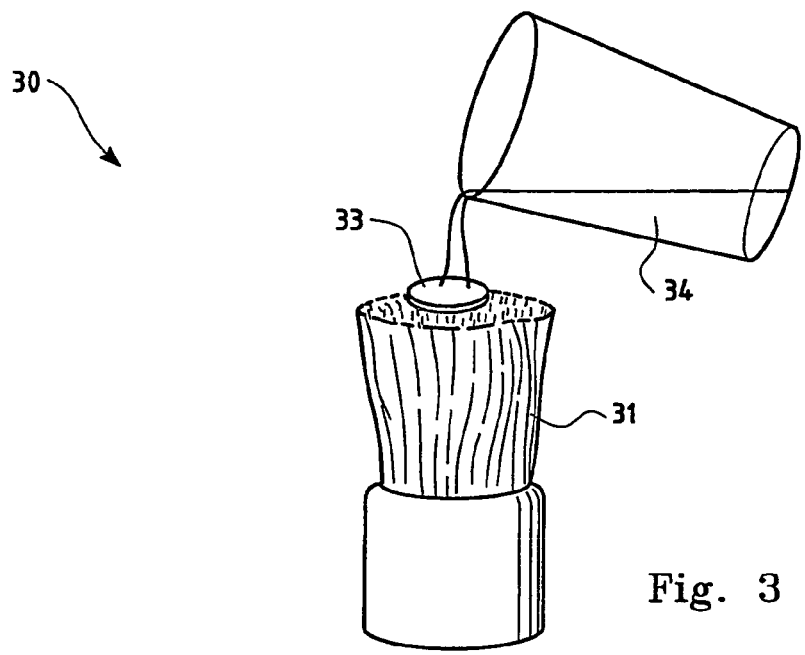
FIG. 3 illustrates an application method according to a third embodiment of the invention.

In a third preferred embodiment of the invention with reference to FIG. 3 wherein is shown an application method 30 wherein solid delivery vehicle 33 is placed on a shaving brush 31 to which water 34 is added to produce a shaving paste. In this embodiment the volume of water is not predetermined but the formation of paste from solid 33 is left to the preference of the user.

Figure 4:
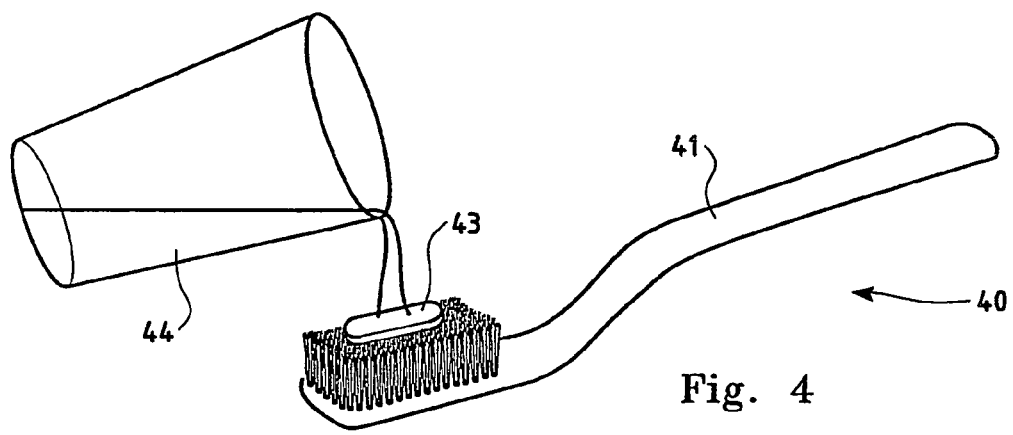
FIG. 4 illustrates an application method according to a fourth embodiment of the invention.

In a fourth preferred embodiment of the invention with reference to FIG. 4 wherein is shown an application method 40 wherein solid delivery vehicle 43 is placed on a toothbrush 41 to which water 44 is added to form toothpaste.

Figure 5:
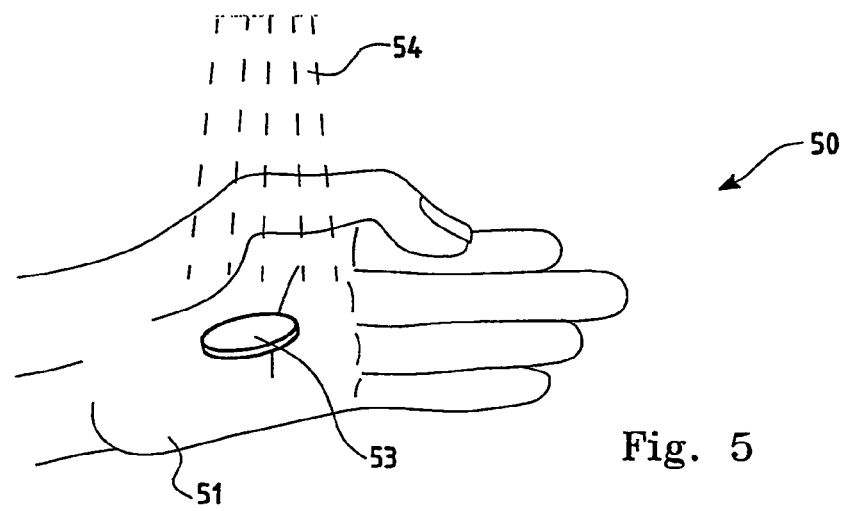
FIG. 5 illustrates an application method according to a fifth embodiment of the invention.

In a fifth preferred embodiment of the invention with reference to FIG. 5 wherein is shown an application method wherein solid delivery vehicle 53 is placed in the palm of the hand 51. When water 54 is added to the solid it forms a soap paste.

In yet a further preferred embodiment of the invention, a solid according to the invention may be placed in the hand and water added to form a therapeutic paste for treatment of wounds, sunburn, muscular tensions and other trauma.

The above describes only some embodiments of the present invention and modifications, obvious to those skilled in the art, can be made thereto without departing from the scope and spirit of the present invention.

The invention claimed is:

1. A delivery vehicle and treatment agent system for delivering an agent to an animal comprising:
a substantially solid delivery vehicle for application to an animal said delivery vehicle delivered to said animal as a paste;
a delivery device that receives the substantially solid delivery vehicle and water wherein by addition of water to said substantially solid delivery vehicle placed on or in said delivery device results in the substantially solid delivery device being transformed into a paste containing the agent prior to the animal receiving paste;
wherein said solid delivery vehicle including a treatment agent and a water activatable expander; said expander comprising granules of a cross-linked homopolymer of N-vinyl-2-pyrrolidone and wherein the paste is delivered to the animal via the delivery device.

2. The system of claim 1, wherein said granules have an average maximum dimension in the range of 10-100 μm.

3. The system of claim 1 wherein said granules have an average maximum dimension in the range of 20-80 μm.

4. The system of claim 1, wherein said granules have an average maximum dimension in the range of 30-60 μm.

5. The system of claim 1, wherein said expander comprises 30-50% by weight of vehicle.

6. The system of claim 1, wherein, said expander comprises 40-50% by weight of vehicle.

7. The system of claim 1, wherein a ratio by weight of said expander to the total combined weight of said vehicle is determined by a desired volume of paste.

8. The system of claim 1, wherein the treatment agent is therapeutic.

9. The system of claim 1, wherein the treatment agent is nutritional.

10. The system of claim 1, wherein the treatment agent is hygienic.

11. The system of claim 1, wherein the treatment agent is cosmetic.

12. The system of claim 1, wherein the treatment agent is applied by a dosing syringe.

13. The system of claim 1, wherein the treatment agent is configured for topical application.

14. The system of claim 1, wherein the treatment agent is ingestible.

15. The system of claim 1, wherein the paste is delivered to an animal by means of one of a group of delivery devices consisting of a dosing syringe, a spoon, a shaving brush, a tooth brush and a hand.

* * * * *